(12) United States Patent
Nongaillard et al.

(10) Patent No.: US 8,720,274 B2
(45) Date of Patent: May 13, 2014

(54) DEVICE AND METHOD FOR STUDYING A STUDY AREA BY MEANS OF AN ACOUSTIC WAVE

(75) Inventors: Bertrand Nongaillard, Wallers (FR); Pierre Campistron, Mons En Baroeul (FR); Julien Carlier, Sameon (FR); Dorothée Debavelaere-Callens, Sameon (FR); Georges Nassar, Raismes (FR); Fabrice Lefebvre, Artres (FR)

(73) Assignee: Centre National de la Recherche Scientifique, Paris (FR)

( * ) Notice: Subject to any disclaimer, the term of this patent is extended or adjusted under 35 U.S.C. 154(b) by 272 days.

(21) Appl. No.: 13/141,200

(22) PCT Filed: Dec. 15, 2009

(86) PCT No.: PCT/FR2009/052546
§ 371 (c)(1),
(2), (4) Date: Sep. 16, 2011

(87) PCT Pub. No.: WO2010/072944
PCT Pub. Date: Jul. 1, 2010

(65) Prior Publication Data
US 2011/0314920 A1    Dec. 29, 2011

(30) Foreign Application Priority Data

Dec. 22, 2008 (FR) ..................................... 08 07357

(51) Int. Cl.
*G01N 29/22*    (2006.01)
(52) U.S. Cl.
USPC ........................................................ 73/649
(58) Field of Classification Search
CPC ............ G01N 29/022; G01N 29/2462; G01N 29/0522
USPC ..................... 73/649, 61.41, 61.75, 618, 632
See application file for complete search history.

(56) References Cited

U.S. PATENT DOCUMENTS 5,853,994 A    12/1998    Gopinathan et al.
5,895,199 A *  4/1999    Baumert et al. .............. 414/686

(Continued)

FOREIGN PATENT DOCUMENTS

| EP | 1 878 483 A1 | 1/2008 |
| FR | 2 791 137 A1 | 9/2000 |
| FR | 2 882 205 A1 | 8/2006 |

OTHER PUBLICATIONS

International Search Report, dated Mar. 12, 2010, from corresponding PCT application.

*Primary Examiner* — J M Saint Surin
(74) *Attorney, Agent, or Firm* — Young & Thompson (57) ABSTRACT

A device includes a substrate 5, an emission source 1 emitting an acoustic beam from the first surface 7 of the substrate 5 towards the second surface 6 of the substrate 5, first reflection element 11 arranged so that, after reflection, the beam has a propagation direction substantially parallel to the second surface 6 and through a study area 3, and second reflection element 12 for reflecting the beam after crossing the study area 3 in the direction of the first surface, towards a receiver 10. The device is useful in the field of bioMEMS and labs-on-a-chip, and in particular makes it possible to leave one of the surfaces of the substrate free, for example for observation of the study area in parallel by element of an optical microscope. Moreover, the device facilitates the production of elements for the focussing or divergence (lenses) or reflection (mirror) of the acoustic beam.

29 Claims, 3 Drawing Sheets

(56) References Cited

U.S. PATENT DOCUMENTS

| | | | |
|---|---|---|---|
| 6,033,546 A * | 3/2000 | Ramsey | 204/603 |
| 6,082,181 A | 7/2000 | Greenwood | |
| 6,210,128 B1 * | 4/2001 | Rife et al. | 417/322 |
| 6,568,052 B1 * | 5/2003 | Rife et al. | 29/25.35 |
| 6,948,843 B2 * | 9/2005 | Laugharn et al. | 366/127 |
| 7,968,049 B2 * | 6/2011 | Takahashi et al. | 422/20 |
| 2003/0029242 A1 | 2/2003 | Yaralioglu et al. | |
| 2008/0211602 A1 | 9/2008 | Khelif et al. | |

* cited by examiner

DEVICE AND METHOD FOR STUDYING A STUDY AREA BY MEANS OF AN ACOUSTIC WAVE

TECHNICAL FIELD

The present invention relates to a device and a method for studying a study area by means of an acoustic wave.

The field of the invention is more particularly but not limitatively that of bioMEMS (bio-MicroElectroMechanical-System) and labs-on-a-chip or that of the integration of acoustic components on wafers, electronic and microfluidic components, guided and localized acousto-optic interactions and the study of phonic networks on wavelength scales of the order of a micron.

The invention responds in particular to a growing demand from biologists to have integrated sensors providing dynamic information on mechanical properties of biological cells.

STATE OF THE PRIOR ART

Usually, the production of acoustic components on a wafer or thin substrate requires the deposition of at least one acoustic beam emission source on a first surface of a thin substrate, which leads to a constraint on the propagation direction of the bulk waves engendered.

Figure 1:
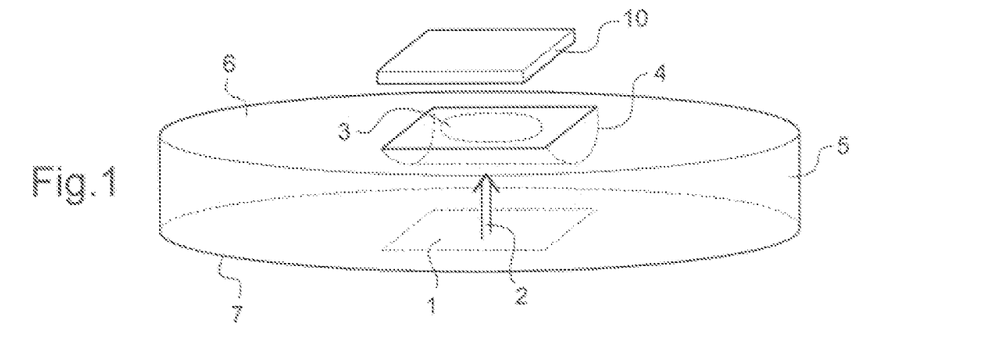
FIG. 1 illustrates a perspective view of a first embodiment of the device according to the prior art.

A first solution of the state of the prior art illustrated in FIG. 1 consists of studying a study area situated in said substrate by means of the acoustic beam emitted by the emission source situated on the first surface of said substrate. A receiver is then situated on a second surface of the same substrate, generally in lamellar form, the first and second surfaces being substantially opposite each other and parallel. Such a technical solution means that the first and the second surfaces are occupied, one by the emission source, the other by the receiver. The emission source, the receiver and the study area are aligned.

It is often useful, in addition to the measurement by the acoustic beam, to carry out another type of measurement on the study area. This other type of measurement, for example via an observation of the study area, requires the first or the second surface, preferably the second surface, to be free so as to be able to have a second observation device such as an optical microscope above the study area, aimed at the second surface.

Figure 2:
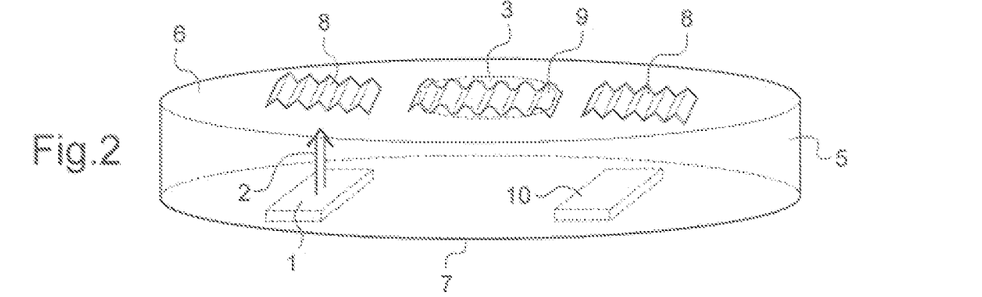
FIG. 2 illustrates a perspective view of a second embodiment of the device according to the prior art.

A second solution according to the prior art illustrated in FIG. 2, making it possible to leave the second surface free, then consists of having on the second surface, on either side of the study area, combs or networks of lines with, for example, triangular or rectangular profiles and at intervals equal to the wavelength of a created surface wave. On reaching the second surface of the substrate, the acoustic wave emitted by the emission source is transformed into an acoustic surface wave. Thus, a surface wave is propagated over the second surface of the substrate, crossing the study area. However, such a solution is reserved for classes of materials that are both expensive and incompatible with certain applications such as biology, in particular when the substrate comprises lithium niobate ($LiNbO_3$) or zinc oxide ($ZnO$). This solution is moreover selective in frequency, and does not make it possible to have a large interaction volume, since it is limited to a wavelength in the thickness below the surface of the substrate.

The purpose of the present invention is to propose a device or a method for studying a study area by means of an acoustic wave, that does not have the drawbacks of the solutions of the state of the art set out above.

DISCLOSURE OF THE INVENTION

This objective is achieved with a device for studying a study area by means of an acoustic wave, comprising a substrate provided with distinct first and second surfaces, characterized in that it comprises:

an emission source arranged to emit an acoustic beam originating from the first surface in the direction of the second surface, first reflection means arranged to reflect said beam originating from the first surface, so that, after reflection, the beam has a propagation direction substantially parallel to the second surface and crosses the study area, second reflection means arranged to reflect the acoustic beam in the direction of the first surface after the beam has crossed the study area, and a receiver arranged to receive said acoustic beam reflected by the second reflection means.

The invention makes it possible to have an acoustic beam with a propagation direction substantially parallel to the second surface of the substrate, and therefore to free the second surface for example to make it possible to easily group together several sensors, and therefore several functions, on the same circuit. In fact, the second surface is left free, which makes it possible to arrange thereon a second device, for example an observation and/or measurement device, for example an optical microscope making it possible to view the study area.

Moreover, the first or second surface can be engraved in order to produce elements thereon for the focussing (such as a lens), divergence (such as a lens) or reflection (such as a mirror) of the acoustic beam, these elements having an invariant form along an invariance axis perpendicular to the first or second surface, which considerably facilitates their production by standard lithography methods.

In a preferred embodiment, the emission source is situated on the first surface of said substrate. By contrast, in another embodiment, there may be an intermediate layer between the emission source and the first surface of the substrate.

Similarly, in a preferred embodiment, the receiver is preferably situated on the first surface of said substrate. By contrast, in another embodiment, there may be an intermediate layer between the receiver and the first surface of the substrate.

After reflection by the second reflection means, the acoustic beam the propagation direction of which is parallel to the second surface may be closer to the first surface than to the second surface, or may be closer to the second surface than to the first surface.

Preferably, the first and second surfaces are opposite each other, the substrate being for example parallelepipedic in form or having for example the form of a disc.

In a preferred embodiment, the first and second surfaces are substantially parallel. Preferably, the substrate is presented in the form of a thin strip the two opposite faces of which for example having the larger areas constitute said first and second surfaces.

The first and/or second reflection means of the device according to the invention preferably comprise a mirror formed by an interface of materials, preferably by an interface with the substrate, preferably an air/substrate interface. Thus, a simple difference in index between two materials at the level of an inclined mirror creates a deflection of the acoustic beam emitted by the emission source towards the first reflection means. This difference in index is for example the difference between the index of the substrate and the index of the air, if the substrate is immersed in air, but can also for example be the difference between the index of the substrate and the index of a liquid in which said substrate is immersed. The device according to the invention can also comprise at least one additional layer of material or a set of several additional layers of different superimposed materials, this layer or these layers being arranged on the substrate, so that the first and/or the second reflection means comprise a mirror formed by an interface of materials between the substrate and this additional layer or this set of several additional layers. Each additional layer is preferably selected from: a layer of metal such as preferably copper, zinc, tin, titanium, or a layer of dielectric material, preferably comprising silicon, preferably a silicon oxide such as silicon monoxide SiO or silica $SiO_2$. The thickness of each additional layer is preferably comprised between 0.1 micrometer and 10 micrometers, more preferentially between 0.5 micrometers and 5 micrometers.

The substrate is for example silicon-based. It can be pure silicon, or an alloy or mixture comprising in particular silicon. The substrate can also non-limitatively comprise metal, glass, or a solidified polymer such as polydimethylsiloxane (PDMS).

According to a preferred embodiment, the first and/or second reflection means of the device according to the invention comprise a recess formed on the second surface of the substrate. Each recess is preferably engraved in the second surface of the substrate, and preferably forms an interface with respect to the second surface, which interface acts as an inclined mirror. Thus, the deflection of the acoustic beam is created not only by a difference in index, but also by the surface state of the substrate, for example its local inclination with respect to the acoustic beam.

The first and/or second reflection means preferably comprise a mirror inclined at 45° with respect to the second surface. By mirror is meant, for example, an interface between two materials with different indices. This interface is preferably inclined at 45°, so as to deflect the acoustic beam typically by an angle of 90°, or more generally by an angle equal to twice the acute angle between the acoustic beam and the normal to the mirror. It is important to note this is a reflection and not a transformation of an incident wave into a surface wave. In this sense, the device according to the invention differs from the second solution according to the prior art, in which the wave being propagated in a direction substantially parallel to the second surface is only a surface wave.

Preferably, the emission source and/or the receiver comprise piezoelectric transducers. Piezoelectricity is the property possessed by certain bodies, of becoming electrically polarized under the action of a mechanical stress and reciprocally becoming deformed when an electric field is applied to them. Thus, the acoustic wave being linked to the notion of mechanical stress or vibration, a piezoelectric transducer serves as an acoustic wave emission source, converting a voltage into a mechanical stress, and as a receiver converting a mechanical stress into a voltage.

According to a preferred embodiment, the study area comprises part of a microfluidic channel preferably situated on the second surface. It is thus possible to non-destructively and dynamically characterize the mechanical properties of a biological cell passing through this microfluidic channel and reached by the acoustic beam.

According to a preferred embodiment, the device comprises at least one lens of a given form or curvature for example cylindrical or parabolic, each lens being arranged in order to be passed through by the acoustic beam. Preferably, the form or curvature of the at least one lens does not vary along an axis substantially perpendicular to the second surface, this axis hereafter being referred to as the invariance axis. In one embodiment, the device according to the invention can comprise two lenses, a first lens being situated on the path of the acoustic beam between the first reflection means and the study area, a second lens being situated on the path of the acoustic beam between the study area and the second reflection means. In a variant, the device according to the invention can comprise only one of these two lenses. In another embodiment, the device according to the invention can comprise a concave lens, the study area being situated in the middle of the concave lens. Preferably, the at least one lens has the form of a portion of a cylinder the axis of revolution of which is substantially perpendicular to the second surface. Such a geometry has advantages in terms of ease of manufacture, in particular by lithography methods. In fact, in this case, if the device according to the invention is compared with the first solution according to the prior art, the direction of the invariance axis of the lens in the device according to the invention has the advantage of being adapted to the plane of maximum resolution of the engraving devices, namely the planes parallel to the surface of the substrate. Here, these are the planes parallel to the second surface of the substrate. According to the invention, it can be seen that the radius of curvature of the at least one lens can then be engraved with precision, whereas according to the prior art, a cylindrical lens would have an axis parallel to the second surface of the substrate and the radius of curvature of this cylindrical lens would then be engraved step by step, gradually varying the engraving heights in the substrate. The engraving is then carried out with less precision.

The arrangement of the second surface according to the invention also makes it possible, for the same reason, to simply and precisely engrave pillar or membrane type elements in the microfluidic channel so as for example to obscure part of the incident or transmitted acoustic beam, or to excite one of the vibration modes of these elements by radiation pressure.

The at least one lens is preferably formed directly in the substrate, so as to maintain continuity of material from the emission source up to the study area in particular in order to limit energy losses. A lens the form or curvature of which does not vary along an axis substantially perpendicular to the second surface is advantageous as it makes it possible both to concentrate the energy on a reduced surface area which increases the resolution on the measurements in the study area, and to scan the study area using an acoustic beam focussed on a segment, which increases the probability of detecting for example a molecule or a cell passing through the microfluidic channel compared with the case of focussing on a point. It is nevertheless possible to envisage using a spherical lens, which then focuses the acoustic beam substantially on a point, but the engraving of which would be more complicated.

If the study area is part of a microfluidic channel, the at least one lens is preferably formed in a wall of the microfluidic channel. Thus, a particularly compact device is produced since a recess is simply made in the form of a portion of a cylinder, in at least one wall of the microfluidic channel situated facing the study area.

According to a certain embodiment, the first reflection means are distinct from the second reflection means, and the emission source is preferably distinct from the receiver. In this embodiment, the acoustic beam is emitted by the emission source, reflected by the first reflection means, crosses the study area in the substrate, and is then reflected by the second reflection means towards the receiver. This is referred to as working in transmission, as the study area is studied as a function of a beam that is transmitted inside this area.

According to another embodiment, the first and second reflection means are merged. This is referred to as working in reflection. According to this embodiment, the emission source and the receiver are preferably also merged. Thus, the emission source emits the acoustic beam in the direction of the first reflection means, then the acoustic beam is reflected by the first reflection means, then it penetrates inside the study area. There, either the device also comprises third reflection means arranged to reflect the beam towards the second reflection means (merged with the first reflection means) after the beam has passed through at least part of the study area, or the study area is arranged to reflect the beam towards the second reflection means. In this second case, the acoustic beam is for example reflected on a cell or molecule or other element passing through the microfluidic channel. It should be noted that it is moreover possible to work in reflection without the first and second reflection means being merged. A simple angular offset between the optical axes of the first reflection means, third reflection means and second reflection means for example makes it possible for the beams incident and reflected on the study area not to be aligned, and therefore for the first and second reflection means not to be merged. In this case, the emission source and the receiver are not necessarily merged either.

In a preferred embodiment, the second reflection means and the receiver are arranged in order to receive a beam diffracted in the study area. The device can in this case comprise several assemblies each comprising second reflection means and a receiver, a first assembly making it possible to study the acoustic beam in transmission, substantially in the alignment of the incident beam in the study area, at least one other assembly making it possible to study the part of the acoustic beam diffracted by the study area. The device can comprise either only the second reflection means and the receiver substantially in alignment with the incident beam in the study area, or only the second reflection means and the receiver substantially aligned with the beam diffracted by the study area, or several reflection means and several receivers in order to study both the beam transmitted substantially without angular offset with respect to the incident beam in the study area and at least one order of diffraction in the study area. The study both of the transmitted beam and of at least one diffracted beam makes it possible to have different contrasts in the study area, and to retrieve more information on the latter. Such a device in which the second reflection means are for example inclined with respect to the axis of the microfluidic channel also allows for the study of a beam diffracted in the study area, and the study of other types of beams deflected in the study area, for example the study of a beam diffused in the study area.

According to another embodiment, the device comprises several emission sources and several receivers, each receiver being associated with one of the emission sources and being arranged to receive an acoustic beam: said beam being emitted from the first surface and in the direction of the second surface by the emission source with which it is associated, then reflected by the first reflection means so that, after reflection, the beam has a propagation direction substantially parallel to the second surface and crosses the study area, then reflected by the second reflection means in the direction of the first surface after having crossed the study area.

According to a first associated embodiment, the emission sources are aligned so that different acoustic beams emitted by the different sources cross the study area at different heights. Each emission source allows for the study of a given height of the study area or of the substrate. It is thus possible to analyze different heights for example of the microfluidic channel, but also to produce an interference contrast by leaving part of the transmitted beam below the microfluidic channel. For reception, several receivers are arranged in line, each preferably receiving a beam emitted by a corresponding emission source.

According to another embodiment, the projections of the emission sources and of the receivers on a plane parallel to the second surface and crossing the study area are distributed around the study area. Preferably, the first reflection means are then constituted by at least one mirror surrounding part of the study area, have for example the form of at least one arc of a circle centred on the study area, and make it possible to reflect the acoustic beams emitted by all the emission sources. Similarly, the second reflection means are preferably constituted by at least one mirror surrounding part of the study area, having for example the form of at least one arc of a circle centred on the study area, and making it possible to reflect the acoustic beams towards all the receivers. Such an embodiment makes it possible to study the transmitted beam and/or the reflected beam as a function of an angle for example between the acoustic beam reflected by the first reflection means and the direction of flow in the microfluidic channel.

Preferably, the first and/or second reflection means comprise at least one curved mirror. Preferably, the form or curvature of the at least one curved mirror does not vary along an axis substantially perpendicular to the second surface. In fact, according to an advantageous embodiment, several emission sources are arranged preferably in line, so that the total acoustic beam reflected by the first reflection means is enlarged along an axis substantially perpendicular to the invariance axis of at least one lens and/or along an axis substantially parallel to the invariance axis of the at least one lens. Thus, it is possible to direct all the more energy towards the study area. It is then advantageous to concentrate this energy, in particular by means of the focussing action of the at least one lens. However, the operator is relatively limited for concentrating this energy. In fact, the at least one lens being preferably formed in a side wall of a microfluidic channel, the radius of curvature of said at least one lens is fixed by the width of the microfluidic channel. This leads to a determined pupil diameter D. By preferably using the first and/or second reflection means comprising a curved mirror, it is possible to combine the action of at least one curved mirror with the action of a lens. The at least one curved mirror makes it possible to reduce the diameter of the acoustic beam incident on a lens in order to adapt this diameter to the pupil diameter D. The at least one curved mirror is for example a cylindrical mirror, a parabolic mirror, or of a form optimized in order to minimize geometric aberrations. Besides the energy concentration, an additional advantage of this at least one curved mirror relates more particularly to the embodiment in which different acoustic beams cross the study area at different heights. The production of a network of N emission sources provides access to selective acoustic information as a function of the height z in the study area. This leads to an elementary height for each of the emission sources equal to P/N, where P represents the maximum height of the study area. The surface area of the emission sources is then preferably fixed at $D*P/N$, which surface area can lead to electric impedances completely different from and generally greater than the characteristic impedance (often $50\Omega$). It is therefore particularly advantageous to be able to further concentrate energy at each altitude z in the study area. Whereas a lens the form or curvature of which does not vary along an axis substantially perpendicular to the second surface only concentrates the energy mainly on an axis parallel to its invariance axis, the at least one curved mirror makes it possible to also concentrate the energy on an axis perpendicular to its invariance axis. Preferably, two curved mirrors are used, arranged afocally so as to obtain a magnification greater than one between the acoustic beam originating from the emission source and the acoustic beam incident on the lens. The possibility of producing the at least one curved mirror is a direct consequence of the propagation direction of the acoustic beam, after reflection on the first reflection means, substantially parallel to the second surface. Thus, it is possible to concentrate more energy on a smaller surface area, inside the study area.

According to another aspect of the invention, a method according to the invention is proposed for studying a study area by means of an acoustic wave, implemented by a device according to the invention, and characterized in that it comprises the emission of an acoustic beam originating from a first surface of a substrate in the direction of a second surface of this substrate, the first and second surfaces being distinct, a first reflection by first reflection means, said first reflection reflecting said beam originating from the first surface, so that the beam has, after reflection, a propagation direction substantially parallel to the second surface and crosses the study area, a second reflection by second reflection means, said second reflection reflecting the acoustic beam in the direction of the first surface after the beam has crossed the study area, and the reception, by a receiver, of the acoustic beam reflected by the second reflection means.

The method according to the invention can also comprise the passing of the acoustic beam through at least one lens, each lens being arranged to be passed through by the acoustic beam between the first reflection means and the study area and/or between the study area and the second reflection means.

The method according to the invention can also comprise the reception, by the second reflection means and by the receiver, of an acoustic beam diffracted in the study area.

The method according to the invention can comprise several emissions of acoustic beams by several sources and several receptions of acoustic beams by several receivers, each receiver being associated with one of the emission sources and receiving an acoustic beam emitted by the emission source with which it is associated, then reflected by the first reflection means, then reflected by the second reflection means after having crossed the study area. Preferably, the different acoustic beams emitted by the different emission sources cross the study area at different heights.

DESCRIPTION OF THE FIGURES AND EMBODIMENTS

Other advantages and features of the invention will become apparent on reading the detailed description of implementations and embodiments that are in no way limitative, and the following attached drawings.

FIG. 1 illustrates a first embodiment according to the prior art in which an emission source 1 emits an acoustic beam represented by the arrow 2 through a substrate 5 from the first surface 7 of this substrate towards the second surface 6 of this substrate. The acoustic beam then crosses a study area 3 with a dotted outline. FIG. 1 also represents a cylindrical lens 4 formed in the substrate 5. The planes of maximum resolution of the engraving devices making it possible in particular to form the cylindrical lens 4 are planes parallel to the second surface 6 of the substrate 5. It can therefore be seen in FIG. 1 that in the first embodiment according to the prior art, the orientation of the cylindrical lens 4 is not optimal with respect to this plane and that the latter must be formed by successive engravings in planes parallel to the second surface 6. This first embodiment according to the prior art has the major drawback of not leaving the second surface 6 free since a receiver 10 would have to be placed above the second surface 6, which prevents measurements and/or observations of the study area 3 other than those carried out by means of the acoustic beam. In this case, the substrate 5 is for example lithium niobate ($LiNbO_3$) or zinc oxide ($ZnO$).

FIG. 2 illustrates a second embodiment according to the prior art, in which the emission source emits an acoustic beam represented by the arrow 2 from the first surface 7 in the direction of the second surface 6. Networks of lines 8 with triangular profiles and at intervals equal to the wavelength of the surface wave are arranged on both sides of the study area 3. After the arrival of the acoustic beam on the network of lines 8 situated on the side of the emission source 1, a surface wave 9 is propagated over the second surface 6 of the substrate 5, crossing the study area 3. Such a solution is non-biocompatible, and also has a very poor energy yield, since only surface waves are used in the study area, instead of the main acoustic beam. Moreover, in this embodiment the height of the interaction volume is limited to a wavelength under the surface 6 of the substrate 5.

FIGS. 3 to 8 show different embodiments of the device according to the invention implementing a method according to the invention. Each of these embodiments comprises a substrate 5 provided with a first surface 7 and second surface 6, and an emission source 1 for emitting an acoustic beam from the first surface 7 in the direction of the second surface 6. The substrate is in the form of a thin strip in which the first surface 7 is parallel to the second surface 6. The beam emitted in the direction of the second surface 6, before reaching the first reflection means 11, has a propagation direction perpendicular to the first surface 7 and to the second surface 6. The acoustic beam is represented by the arrows 2. The first reflection means 11 are arranged in order to reflect the acoustic beam originating from the emission source 1 so that the beam has, after reflection, a propagation direction substantially parallel to the second surface 6 and crosses the study area 3. Second reflection means 12 are arranged in order to reflect the acoustic beam in the direction of the first surface 7 after the beam has crossed the study area 3. The beam reflected by the second reflection means 12 has a propagation direction perpendicular to the second surface 6 and to the first surface 7. A receiver 10 is arranged to receive the beam reflected by the second reflection means 12. The substrate is made of silicon. The emission source 1 is situated on the first surface 7. The receiver 10 is situated on the first surface 7.

It should be noted that according to the invention, the reflection of the acoustic beam does not change the nature of this beam but changes its direction. In particular, the beam emitted is a bulk wave, and remains a bulk wave after reflection by the first or second reflection means 11, 12.

The emission source 1 is situated on the first surface 7. The receiver 10 is itself also situated on the first surface 7.

The emission source 1 and the receiver 10 comprise piezoelectric transducers. The surface area of a piezoelectric transducer is for example ten thousand square micrometers. A piezoelectric transducer is often presented in the form of a bar, for example with a main surface substantially parallel to the first surface 7 with dimensions of one hundred micrometers times one hundred micrometers, and with a height of three micrometers. The study area 3 comprises part of a microfluidic channel 13 engraved along the second surface 6 and through which pass in particular biological cells 14, and with a height of one hundred micrometers. The width l of the microfluidic channel 13 is for example one hundred micrometers, not including the thickness of the lenses 4.

Each of the reflection means 11 or 12 shown in the figures comprises a simple air/substrate interface engraved in the second surface 6 of the substrate 5.

Each interface is formed by a recess. The recess is in this case substantially in the form of a prism, the base of which is substantially parallel to the second surface 6 and comprising two faces inclined substantially at 45° with respect to the second surface 6. One of the faces forms a mirror inclined at 45° with respect to the second surface 6. The prism has for example a length L that measures one hundred micrometers and a height h that measures one hundred micrometers. It can be seen in particular in FIG. 7 that the edge formed by the two faces of the prism inclined at 45° with respect to the second surface 6 do not necessarily meet directly but can be linked by an additional face 14 for example substantially parallel to the second surface 6.

For a frequency of the Gigahertz order in a silicon substrate, the wavelengths used by the acoustic beam are of the micrometer order, for example eight to nine micrometers. At these orders of magnitude, the surface of the reflection means 11 and 12 does not require a very high polishing, in contrast to the needs when working for example with light beams in the visible range.

The receiver 10 is linked to analysis means that exploit the electric signal generated by the receiver in response to the acoustic beam received, and calculate different pieces of information from this signal. For example, these analysis means can be arranged in order to process the amplitude and the phase of the acoustic beam received by the receiver, in order to quantify a speed of propagation of the acoustic beam in the study area and/or an absorption of the acoustic beam in the study area, then determine a coefficient of transmission or acoustic reflection of the objects (biological cells) crossing the study area or elastic properties of these objects. The processing of the acoustic beam received typically comprises frequency amplification and filtering. The analysis means typically comprise a computer equipped with an acquisition adapter for the signal generated by the receiver, or a dedicated analogue or digital circuit. For these different stages of processing, quantification and determination, it is possible for example to implement methods or algorithms as described in the following references:

C. F. Quate, A. Atalar and H. K. Wickramasinghe, Acoustic microscopy with mechanical scanning—A review, Proc. IEEE, vol. 67, No. 8, pp 1092-1113, 1979

B. Hadimioglu and C. F. Quate, Water acoustic microscopy at suboptical wavelengths, Appl Phys Lett, vol. 43, pp 1006-1007, 1983

Figure 3A:
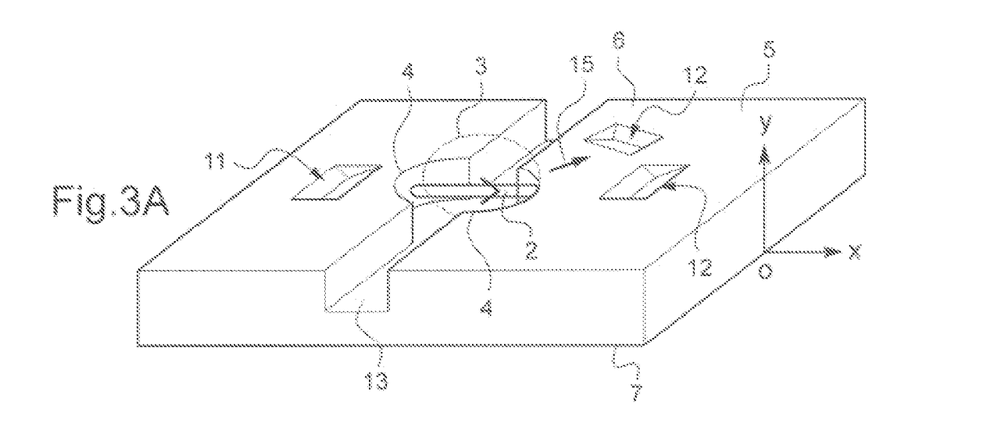
FIG. 3A illustrates a perspective view of a first embodiment of the device according to the invention.
Figure 3B:
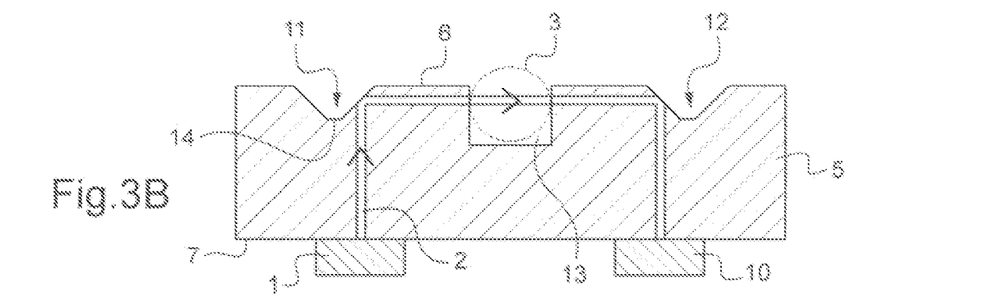
FIG. 3B illustrates a cross-sectional profile view along the axis MN of the first embodiment of the device according to the invention.

FIGS. 3A and 3B show a first embodiment, in which work is carried out in transmission. In this case, the first and second reflection means 11 and 12 are distinct, similarly the emission source 1 and the receiver 10 are distinct. It can also be seen in FIG. 3A that this embodiment comprises two second reflection means 12: one aligned with the emergent beam substantially without angular offset from the first reflection means 11 for studying the study area 3 in transmission, and the other aligned with the diffracted beam represented by the arrow 15 for studying the study area 3 in diffraction. There are therefore in the device according to FIGS. 3A and 3B two receivers 10, one for receiving the diffracted beam, the other for receiving the beam having crossed the study area 3 substantially without angular offset. It is also possible to imagine a device in which only the beam diffracted in the study area 3 would be studied, or by contrast only the beam transmitted substantially without angular offset. It can also be seen in FIG. 3A that two cylindrical lenses 4 are formed in the substrate 5 on the path of the acoustic beam to be passed through by the acoustic beam, a first lens between the first reflection means 11 and the study area 3, a second lens between the study area 3 and the second reflection means 12. The radius of curvature of the cylindrical lenses 4 is for example one hundred micrometers, and their height is for example one hundred micrometers. The two cylindrical lenses 4 are formed directly by a deformation of part of the side walls of the microfluidic channel 13. Such a device is therefore particularly compact: it has few interfaces and therefore low energy losses. Each cylindrical lens 4 has the form of a portion of a cylinder the axis of revolution of which is perpendicular to the first surface 7 and to the second surface 6, this axis of revolution being an invariance axis along which the form and the curvature of this lens 4 do not vary.

Figure 4:
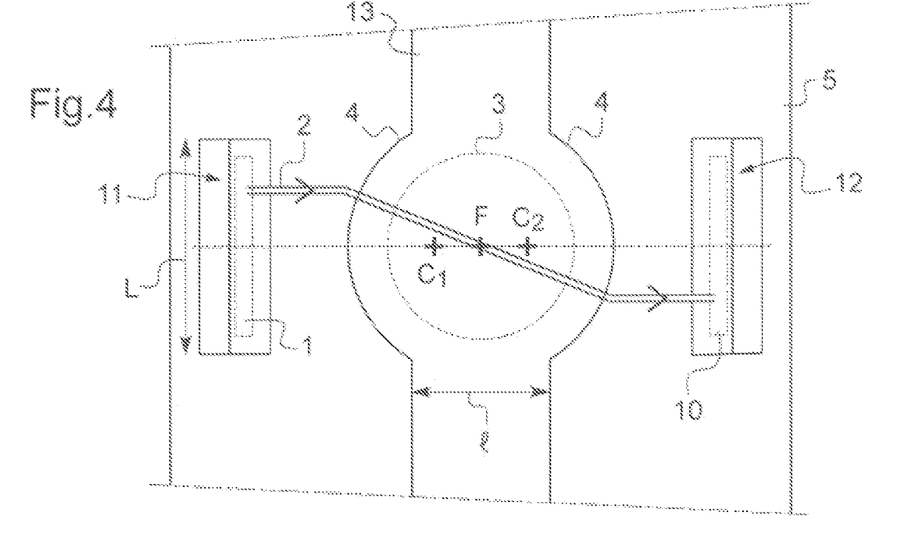
FIG. 4 illustrates a top view of a second embodiment of the device according to the invention.

FIG. 4 is a top view of a second embodiment of the device according to the invention that is described only for its differences with respect to the first embodiment in FIGS. 3A and 3B, and in which the study area 3 is studied only by means of the beam transmitted substantially without angular offset. In FIG. 4, $C_1$ represents the centre of curvature of the first cylindrical lens 4, and $C_2$ represents the centre of curvature of the second cylindrical lens 4. F represents the common focal point of the two cylindrical lenses 4. However, the focal points of the two cylindrical lenses 4 are not necessarily merged, although a situation in which the focal points are merged is optimum. The embodiment according to FIG. 4 is afocal: the acoustic beam emitted by the emission source 1 is a parallel beam, this beam is then focussed inside the study area 3 by the first cylindrical lens 4, then it is once again collimated by the second cylindrical lens 4 so that a parallel beam reaches the receiver 10. This configuration makes it possible to focus the energy along a bar substantially parallel to the axis of the two cylindrical lenses 4, situated inside the study area 3, for example, but not necessarily, in the middle of the study area.

Figure 5:
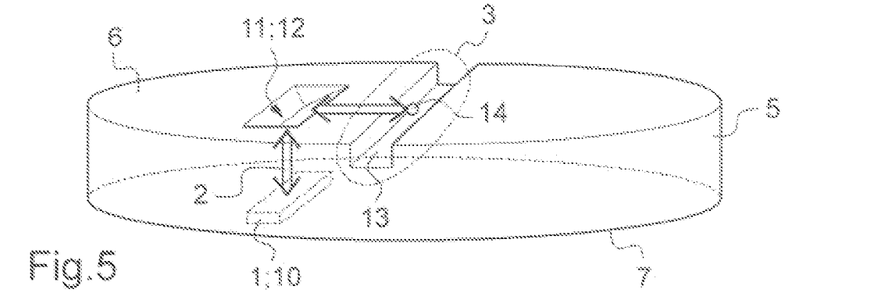
FIG. 5 illustrates a perspective view of a third embodiment of the device according to the invention.

FIG. 5 shows a third embodiment of a device according to the invention that is described only for its differences with respect to the first embodiment in FIGS. 3A, 3B, and in which the study area 3 is studied in reflection. In this case, the first reflection means 11 are merged with the second reflection means 12. The acoustic beam emitted by the emission source 1 then reflected by the first reflection means is reflected in the direction of the second reflection means by the study area 3, for example by a cell 14 situated in this area 3. In a variant which is not shown, the acoustic beam emitted by the emission source 1 then reflected by the first reflection means is reflected in the direction of the second reflection means by third reflection means situated for example on the side of the study area 3 opposite the first reflection means 11, and aligned so as to send an acoustic beam towards the second reflection means 12. Moreover, the receiver 10 and the emission source 1 are merged.

Figure 6:
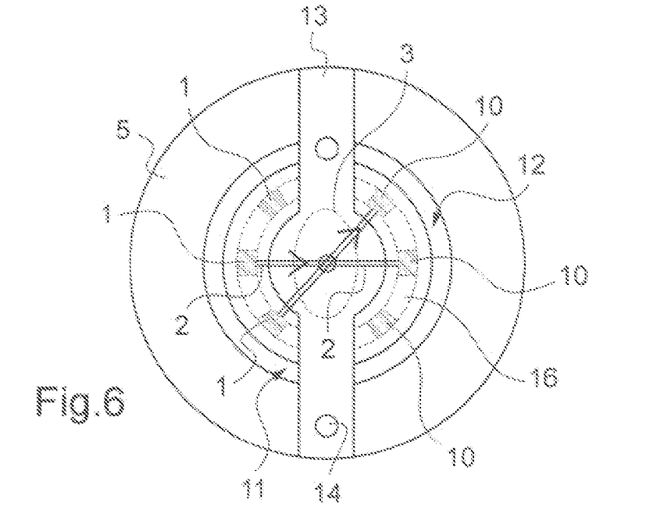
FIG. 6 illustrates a top view of a fourth embodiment of the device according to the invention.
Figure 7:
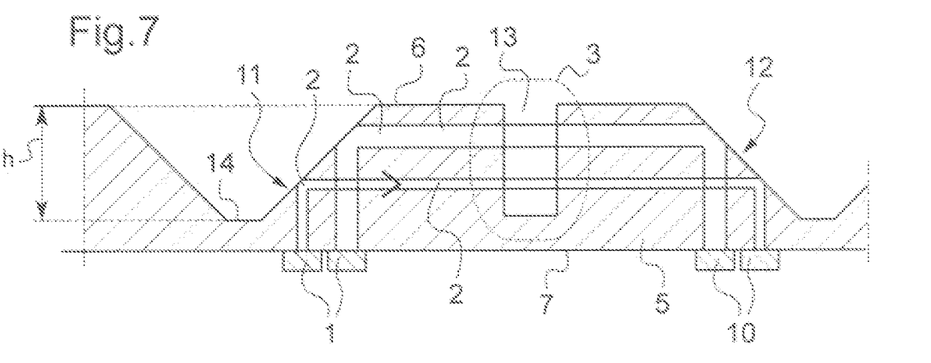
FIG. 7 illustrates a cross-sectional profile view along the plane (Oxy) of a fifth embodiment according to the invention.

FIGS. 6 and 7 illustrate embodiments comprising several emission sources 1 identical to that previously described, and several receivers 10 identical to that previously described. Each receiver 10 is associated with one of the emission sources 1 and is arranged to receive an acoustic beam:

emitted from the first surface 7 and in the direction of the second surface 6 by the emission source 1 with which this receiver is associated, then reflected by the first reflection means 11 so that the beam after reflection has a propagation direction substantially parallel to the second surface 6 and crosses the study area 3, then reflected by the second reflection means 12 in the direction of the first surface 7 after having crossed the study area 3.

FIG. 6 shows a fourth embodiment of a device according to the invention that is described only for its differences with respect to the first embodiment in FIGS. 3A, 3B, and making it possible to study the study area 3 as a function of the angle of incidence of the acoustic beam in the study area 3. The projections of the several emission sources 1 and receivers 10 on a plane parallel to the second surface 6 and crossing the study area 3 are distributed around the study area 3. In FIG. 6, an area 16 marked by dotted lines defines the area in which emission sources 1 and receivers 10 can be situated. The emission sources 1 and the receivers 10 are coupled two by two for example for a study in transmission, so that a receiver 10 is arranged to receive an acoustic beam emitted by a corresponding emission source 1 and reflected successively by the first and second reflection means 11, 12 as described previously. In this embodiment, the first reflection means 11 comprise a single mirror for the different emission sources 1, and the second reflection means 12 comprise a single mirror for the different receivers 10. Of course, the microfluidic channel 13 is cut into the substrate 5, which is why if the emission sources 1 are distributed on both sides of the microfluidic channel 13, the first reflection means 11 are themselves also distributed on both sides of said channel 13, and the same applies to the second reflection means 12. It is possible that some of the emission sources 1 are situated on one side of the channel 13, while other emission sources 1 are situated on the other side of the channel 13. The first and second reflection means 11 and 12 are interchangeable, reflection means being arranged over the whole of the free edge of the microfluidic channel as shown in FIG. 6.

In a variant of this fourth embodiment, the first and second reflection means 11, 12 are merged, and each receiver 10 is merged with the emission source 1 with which it is associated, so that this variant operates in reflection according to the principle described with reference to FIG. 5.

FIG. 7 shows a fifth embodiment of a device according to the invention that is described only for its differences with respect to the first embodiment in FIGS. 3A, 3B, and in which several emission sources 1 and several receivers 10 are aligned on the first surface 7 along a straight line passing through a projection of the study area on the first surface 7. Each source and each receiver has a rectangular form, the axis parallel to the longest sides of these rectangles being parallel to the axis of the prism formed by the first reflection means 11. Thus, the emission sources 1 are aligned so that different acoustic beams emitted by different emission sources 1 cross the study area 3 at different heights of this study area, the height being defined along an axis perpendicular to the first and second surfaces. It is therefore possible to study the study area 3 at different heights. In FIG. 7, the acoustic beams emitted by the different emission sources 1 cross the microfluidic channel 13. It can be seen in FIG. 7 that the thickness of the beams varies substantially from one emission source 1 to the other. In this case this chiefly provides a way of differentiating easily and visually between the two beams. However, the emission sources 1 are not all necessarily identical, and do not necessarily emit beams of identical widths. According to a variant not shown, certain of the emission sources emit an acoustic beam which passes under the microfluidic channel 13. It is thus possible to produce an interference contrast by analyzing both the information provided by at least one acoustic beam that has passed through the microfluidic channel 13 and at least one acoustic beam that has passed under the microfluidic channel 13.

In a variant of this fifth embodiment, the first and second reflection means 11, 12 are merged, and each receiver 10 is merged with the emission source 1 with which it is associated, so that this variant operates in reflection according to the principle described with reference to FIG. 5.

Figure 8:
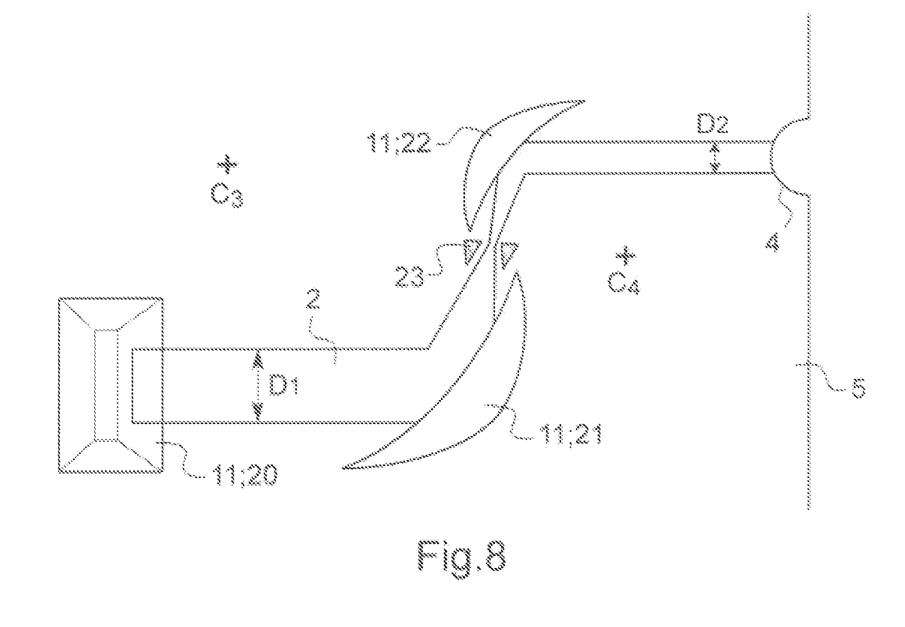
FIG. 8 illustrates a top view of first reflection means comprising a curved mirror.

FIG. 8 shows a detailed top view of a variant of any embodiment of a device according to the invention that has just been described in which the first reflection means 11 comprise at least one curved mirror 21, 22. In the device according to FIG. 8, the acoustic beam represented by the arrow 2 is reflected by a substantially plane mirror 20 inclined at 45° with respect to the second surface 6 of the substrate 5. After reflection on this substantially plane mirror 20, the acoustic beam has a propagation direction substantially parallel to the second surface 6 of the substrate. Two curved mirrors 21 and 22 are arranged afocally. The two curved mirrors 21 and 22 are for example cylindrical, parabolic, or of a form optimized in order to minimize geometric aberrations. The form, in particular the curvature, of each curved mirror 21, 22 does not vary along an axis substantially perpendicular to the second surface. $C_3$ is the centre of curvature or parabolic focal point of the mirror 21. $C_4$ is the centre of curvature or parabolic focal point of the mirror 22. $F_{12}$ is the common focal point of the two curved mirrors 21 and 22. Spatial filters 23 are situated on the path of the acoustic beam, substantially at the level of the common focal point $F_{12}$ of the curved mirrors 21, 22, in order to filter out certain geometric aberrations of the acoustic beam. The acoustic beam incident on the curved mirror 21 has a diameter $D_1$ in a plane substantially parallel to the second surface 6, and a propagation direction substantially parallel to the second surface 6 of the substrate. The incident acoustic beam emergent from the afocal system formed by the curved mirrors 21 and 22 has a diameter $D_2$ in a plane substantially parallel to the second surface 6, and a propagation direction substantially parallel to the second surface 6 of the substrate, where $D_2$ is less than $D_1$. There is therefore a magnification factor $D_1/D_2$ greater than one on the acoustic beam. It is therefore possible to concentrate more energy inside the study area 3 by means of first reflection means 11 comprising a curved mirror. Similarly, if the second reflection means 12 comprise at least one curved mirror 21, 22 according to the same arrangement as that which has just been described for the first reflection means 11, it is possible to simply increase the diameter of the acoustic beam received by the receiver 10 in the same way.

In a variant, the mirror 20 can be a curved mirror and can replace or supplement the mirrors 21, 22.

As described previously, the beam emitted in the embodiments that have just been described is a bulk wave, and remains a bulk wave after reflection by the first or second reflection means 11, 12. In general, there can be three bulk waves in the substrate or propagation media such as silicon:
a compression wave referred to as a longitudinal wave, and two shear waves referred to as transverse waves.

An incidence at 45° of a longitudinal wave on an acoustic mirror in contact with the air, which leads to a mechanically free interface, makes it possible to reflect typically from 10% to 20% of the incident amplitude of a longitudinal wave. The remainder is converted into a shear wave.

Shear waves cannot be used directly for BioMEMS-type applications. The need to use two mirrors in order to develop a measurement system in a microfluidic channel makes it necessary, for BioMEMS, to find a solution in order to improve the longitudinal wave reflection coefficient of the mirrors and reflection means of the device according to the invention.

In other applications, by contrast, it is necessary to improve the transverse wave reflection coefficient of the mirrors and reflection means of the device according to the invention.

Thus, in an improvement of any one of the embodiments that has just been described or any one of the variants that has just been described, for at least one component of (preferably for each component of):
the first reflection means 11,
the curved mirror 21,
the curved mirror 22,
the second reflection means 22, and/or
the third reflection means,
the reflecting surface of this component arranged in order to reflect the acoustic wave comprises one (or preferably several) additional layer(s), each additional layer comprising a material judiciously chosen in order to considerably improve the longitudinal or transverse wave reflection coefficient depending on the use that is made of this wave. More precisely, the first and the second reflection means 11, 12 comprise a mirror formed by an interface of materials with the substrate, and the device according to the invention comprises at least one additional layer of material or preferably a superimposition of several additional layers of different materials arranged on the substrate, so that the first and second reflection means 11, 12 comprise a mirror formed by an interface of materials between the substrate and this additional layer or this superimposition of additional layers.

For each additional layer, there are several possible candidates for materials depending on the performance sought. The following are preferably used:
an additional layer of metal such as preferably copper, zinc, tin, titanium, or a combination of these metal layers, and/or
an additional layer of dielectric material, preferably comprising silicon, preferably a silicon oxide such as silicon monoxide SiO or silica $SiO_2$, or a combination of these layers of dielectric materials.

Each of the additional layers is either deposited by vacuum evaporation, which is the preferred deposition method for an additional metal layer, or by vacuum spraying, which is the preferred deposition method for an additional layer of dielectric material.

The thickness of each additional layer is preferably comprised between 0.1 micrometer and 10 micrometers, more preferentially between 0.5 micrometers and 5 micrometers.

In the variant in which the reflecting surface comprises several additional layers, these additional layers are superimposed on top of each other and are additional layers of different materials. By superimposing several additional layers of different materials, the bandwidth of the reflecting surface is enlarged with respect to the frequency of the acoustic wave reflected by this surface.

In a specific embodiment example, where:
the substrate 5 is made of pure silicon, and each of the reflection means 11 and 12 comprises a simple air/silicon substrate interface formed by a recess and engraved in the second surface 6 of the substrate 5,
each interface reflects a longitudinal acoustic wave having a frequency within a band from 0.1 GHz to 3 GHz, typically 1.6 GHz with an incidence of 45° to the interface,
then each interface typically reflects 10% to 20% of the incident amplitude of a longitudinal wave.

In a first variant, by depositing an additional layer of silica $SiO_2$ with a thickness of 4 μm, on each of the air/silicon interfaces of the first and second reflection means, more precisely on the outside of the substrate 5 i.e. on the air side, the reflection coefficient of each interface becomes substantially equal to 80% for the longitudinal wave within a band from 1.5 GHz to 1.7 GHz, with an incidence of 45° to the interface.

In a second variant, by depositing an additional layer of silica $SiO_2$ with a thickness of 3 μm on each of the air/silicon interfaces of the first and second reflection means, more precisely on the outside of the substrate 5 i.e. on the air side, then an additional layer of titanium with a thickness of 0.5 μm on each of the additional layers of silica, then an additional layer of copper with a thickness of 3 μm on each of the additional layers of titanium, the reflection coefficient of each interface becomes greater than 80% for the longitudinal wave within a band from 1.56 GHz to 2.05 GHz, and with an incidence of 45° to the interface. By increasing the additional layers of different materials, the bandwidth of each of the reflection means is thus improved.

Of course, the invention is not limited to the examples that have just been described and numerous adjustments can be made to these examples without exceeding the scope of the invention. It is moreover possible to combine as desired the different embodiments previously described.

The invention claimed is:

1. A device for studying a study area by an acoustic wave, the device comprising:
a substrate provided with distinct first and second surfaces;
an emission source arranged to emit an acoustic beam originating from the first surface in the direction of the second surface;
first reflection means arranged to reflect said beam originating from the first surface, so that, after reflection, the beam has a propagation direction substantially parallel to the second surface and crosses the study area;
second reflection means arranged to reflect the acoustic beam in the direction of the first surface after the beam has crossed the study area; and
a receiver arranged to receive said acoustic beam reflected by the second reflection means.

2. The device according to claim 1, wherein the emission source is situated on the first surface.

3. The device according to claim 1, wherein the receiver is situated on the first surface.

4. The device according to claim 1, wherein the first and/or second reflection means comprises a mirror formed by an interface of materials.

5. The device according to claim 4, wherein the first and/or second reflection means comprises a mirror formed by an interface with the substrate.

6. The device according to claim 4, wherein the first and/or second reflection means comprises a mirror formed by an air/substrate interface.

7. The device according to claim 4, further comprising at least one additional layer of material or a set of several additional superimposed layers of different materials, the additional layer or additional superimposed layers being arranged on the substrate, so that the first and/or the second reflection means comprises a mirror formed by an interface of materials between the substrate and the additional layer or the set of several additional layers.

8. The device according to claim 7, wherein each additional layer is selected from: a layer of metal comprising at least one of copper, zinc, tin, titanium, or a layer of dielectric material, preferably comprising silicon, preferably a silicon oxide, such as silicon monoxide SiO or silica $SiO_2$.

9. The device according to claim 7, wherein the thickness of each additional layer is comprised of between 0.1 and 10 micrometers, more preferentially between 0.5 and 5 micrometers.

10. The device according to claim 1, wherein the first and/or second reflection means comprises a recess formed on the second surface of the substrate.

11. The device according to claim 1, wherein the first and/or second reflection means comprises a mirror inclined at 45° with respect to the second surface.

12. The device according to claim 1, wherein the emission source and/or the receiver comprise piezoelectric transducers.

13. The device according to claim 1, wherein the substrate is a silicon-based substrate.

14. The device according to claim 1, wherein the study area comprises part of a microfluidic channel situated on the second surface.0

15. The device according to claim 1, further comprising at least one lens, each lens being arranged in order to be passed through by the acoustic beam between the first reflection means and the study area and/or between the study area and the second reflection means, and formed in the substrate.

16. The device according to claim 15, wherein the at least one lens has a form or a curvature that does not vary along an axis substantially perpendicular to the second surface.

17. The device according to claim 15, wherein the at least one lens is formed in a wall of the microfluidic channel.

18. The device according to claim 1, wherein the emission source is distinct from the receiver, and
first reflection means are distinct from the second reflection means.

19. The device according to claim 1, wherein the first and second reflection means are merged.

20. The device according to claim 1, wherein the second reflection means and the receiver are arranged in order to receive a beam diffracted in the study area.

21. The device according to claim 1, further comprising
a plurality of emission sources; and
several a plurality of receivers, each receiver being associated with one of the emission sources and being arranged in order to receive the acoustic beam emitted by the emission source with which the receiver is associated, then reflected by the first reflection means, and then reflected by the second reflection means after having crossed the study area.

22. The device according to claim 21, wherein the emission sources are aligned so that different acoustic beams emitted by the different emission sources cross the study area at different heights.

23. The device according to claim 21, wherein projections of the emission sources and of the receivers on a plane parallel to the second surface and crossing the study area are distributed around the study area.

24. The device according to claim 1, wherein the first and/or second reflection means comprise a curved mirror.

25. A method for studying a study area by an acoustic wave, the method comprising:
emitting an acoustic beam originating from a first surface of a substrate in the direction of a second surface of the substrate, the first and second surfaces being distinct;
reflecting, by first reflection means, the beam originating from the first surface, so that, after reflection, the beam has a propagation direction substantially parallel to the second surface and crosses the study area;
reflecting, by second reflection means, the acoustic beam in the direction of the first surface after the beam has crossed the study area; and
receiving, by a receiver, the acoustic beam reflected by the second reflection means.

26. The method according to claim 25, further comprising passing the acoustic beam through at least one lens, each lens being configured in order to be passed through by the acoustic beam between the first reflection means and the study area and/or between the study area and the second reflection means.

27. The method according to claim 25 further comprising receiving, by the second reflection means and by the receiver, an acoustic beam diffracted in the study area.

28. The method according to claim 25, further comprising emitting a plurality of acoustic beams by a plurality of sources; and
receiving the plurality of acoustic beams by a plurality of receivers, each receiver being associated with one of the emission sources and receiving one of the acoustic beams emitted by the emission source with which the receiver is associated, then reflected by the first reflection means, and then reflected by the second reflection means after having crossed the study area.

29. The method according to claim 28, wherein the different acoustic beams emitted by the different emission sources cross the study area at different heights.

* * * * *

UNITED STATES PATENT AND TRADEMARK OFFICE
CERTIFICATE OF CORRECTION

PATENT NO.       : 8,720,274 B2
APPLICATION NO.  : 13/141200
DATED            : May 13, 2014
INVENTOR(S)      : Nongaillard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 358 days.

Signed and Sealed this

Twenty-ninth Day of September, 2015

Michelle K. Lee
*Director of the United States Patent and Trademark Office*